US011198140B2

United States Patent

(12) United States Patent
Shimba et al.

(10) Patent No.: US 11,198,140 B2

(45) Date of Patent: Dec. 14, 2021

(54) CONCENTRATION DEVICE SUITABLE FOR DIELECTROPHORESIS AND METHOD FOR CONCENTRATING PARTICLES WITH THE SAME

(71) Applicant: Panasonic Intellectual Property Management Co., Ltd., Osaka (JP)

(72) Inventors: Noriko Shimba, Nara (JP); Kazuaki Nishio, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 421 days.

(21) Appl. No.: 16/241,995

(22) Filed: Jan. 8, 2019

(65) Prior Publication Data

US 2019/0134645 A1 May 9, 2019

Related U.S. Application Data

(63) Continuation of application No. PCT/JP2017/010339, filed on Mar. 15, 2017.

(30) Foreign Application Priority Data

Oct. 21, 2016 (JP) ............................ JP2016-206610

(51) Int. Cl.

*B03C 5/00* (2006.01)
*B01L 3/00* (2006.01)
(Continued)

(52) U.S. Cl.

CPC ........ *B03C 5/005* (2013.01); *B01L 3/502715* (2013.01); *B01L 3/502761* (2013.01);
(Continued)

(58) Field of Classification Search

None
See application file for complete search history.

(56) References Cited

U.S. PATENT DOCUMENTS

2004/0011650 A1* 1/2004 Zenhausern ............ B03C 5/026 204/547
2005/0040044 A1* 2/2005 Frenea .................... B03C 5/026 204/643

FOREIGN PATENT DOCUMENTS

JP 2005-506191 3/2005

OTHER PUBLICATIONS

International Search Report of PCT application No. PCT/JP2017/010339 dated May 30, 2017.

* cited by examiner

*Primary Examiner* — J. Christopher Ball
(74) *Attorney, Agent, or Firm* — McDermott Will and Emery LLP

(57) ABSTRACT

Provided is a concentration device suitable for dielectrophoresis. The concentration device comprises a first substrate, a second substrate provided so as to face the first substrate, a flow path formed between the first substrate and the second substrate, a first pillar electrode line disposed in the flow path and including a left-side first pillar electrode L (301L), a right-side first pillar electrode R (301R), and one second pillar electrode B (302B), and a second pillar electrode line disposed in the flow path and including one second pillar electrode A (302A). The value of L3 is not less than 5 micrometers, where L3 is equal to (A1−A2), A1 represents a distance between a second vertex Q2 of the second pillar electrode A and a center point O; and A2 represents a distance between the first vertex Q1 of the second pillar electrode B and the center point O.

8 Claims, 20 Drawing Sheets

301
Q1
301
P1
P2
P1
P2
L1
L2
302
Q2
X
Y

(51) Int. Cl.
*C12N 7/00* (2006.01)
*B03C 5/02* (2006.01)

(52) U.S. Cl.
CPC ................ *B03C 5/026* (2013.01); *C12N 7/00* (2013.01); *B01L 2200/0668* (2013.01); *B01L 2400/0424* (2013.01); *B03C 2201/26* (2013.01); *C12N 2760/16151* (2013.01)

X
Y

X
Y

Force given by alternating voltage (N)

1.5E-13
1E-13
5E-14
0
-5E-14
-1E-13
-1.5E-13

-5 -4 -3 -2 -1 0 1 2 3 4 5

L3_28.3um
L3_5um
L3_0um

Norovirus
10 volts pp

Force given by alternating voltage (N)

1.5E-12
1E-12
5E-13
0
-5E-13
-1E-12
-1.5E-12

-5 -4 -3 -2 -1 0 1 2 3 4 5

L3_28.3um
L3_5um
L3_0um

Influenza Virus
5 volts pp

--- Prior Art ---

CONCENTRATION DEVICE SUITABLE FOR DIELECTROPHORESIS AND METHOD FOR CONCENTRATING PARTICLES WITH THE SAME

BACKGROUND

1. Technical Field

The present invention relates to a concentration device suitable for dielectrophoresis and a method for concentrating particles with the same.

2. Description of the Related Art

FIG. 25 is a duplicate of FIG. 1 included in Patent Literature 1. Patent Literature 1 discloses a dielectrophoresis system of handling dielectric particles, particularly biological cells, which are suspended in a medium and subjected to the action of an alternating electrical field. The distribution of said field is made non-uniform using a regular network (R) of electrodes (E1, E2) which can define local areas (L) where the electrical field is minimum in order to concentrate particles in said local zones (L) as a result of the action of the negative dielectrophoresis forces. The inventive system is characterised in that the network (R) of electrodes (E1, E2) is formed on the surface of a multi-layered support (1). Moreover, said system is characterised in that the electrodes (E1, E2) in the network (R) having the same polarity are linked to a common power supply contact (P1, P2) via two networks (R1, R2) of strip conductors (C1, C2) which are formed at an intermediary level located below the network (R) of electrodes.

CITATION LIST

Patent Literature [Patent Literature 1] Japanese Patent Application Publication No. 2005-506 191

SUMMARY

An object of the present invention is to provide a concentration device suitable for dielectrophoresis and a method for concentrating particles with the same.

The present invention provides a concentration device suitable for dielectrophoresis, comprising:

a first substrate;

a second substrate provided so as to face the first substrate;

a flow path formed between the first substrate and the second substrate;

a first pillar electrode line disposed in the flow path; and a second pillar electrode line disposed in the flow path, wherein the first pillar electrode line and the second pillar electrode line are parallel to an X-axis direction;

the first pillar electrode line and the second pillar electrode line include first pillar electrodes and second pillar electrodes;

each of the first pillar electrodes includes a first vertex P1 and a second vertex P2;

each of the second pillar electrode includes a first vertex Q1 and a second vertex Q2;

a line segment between the first vertex P1 and the second vertex P2 which are included in each of the first pillar electrodes is parallel to the X-axis direction;

a line segment between the first vertex Q1 and the second vertex Q2 which are included in each of the second pillar electrodes is parallel to a Y-axis direction;

the X-axis direction is perpendicular to the Y-axis direction in a top view;

a pillar electrode group is composed of a left-side first pillar electrode L selected from the first pillar electrodes included in the second pillar electrode line;

a right-side first pillar electrode R selected from the first pillar electrodes included in the second pillar electrode line;

a second pillar electrode A selected from the second pillar electrodes included in the first pillar electrode; and a second pillar electrode B selected from the second pillar electrodes included in the second pillar electrode;

the left-side first pillar electrode L and the right-side first pillar electrode R are adjacent to each other in a top view in such a manner that the second vertex P2 of the left-side first pillar electrode L and the first vertex P1 of the right-side first pillar electrode R face each other;

a line which passes through the second vertex Q2 of the second pillar electrode A and the first vertex Q1 of the second pillar electrode B is parallel to the Y-axis direction; and the following mathematical formula (I) is satisfied:

$$L3 \geq 5 \text{ micrometers} \quad \text{(I)}$$

where $$L3 = A1 - A2,$$

A1 represents a distance between the second vertex Q2 of the second pillar electrode A and a center point O;

A2 represents a distance between the first vertex Q1 of the second pillar electrode B and the center point O;

the center point O is an intersection point of a line segment P and a line segment Q, the line segment Q is a line segment between the second vertex Q2 of the second pillar electrode A and the first vertex Q1 of the second pillar electrode B; and the line segment P is a line segment between the second vertex P2 of the left-side first pillar electrode L and the first vertex P1 of the right-side first pillar electrode R.

The present invention provides a concentration device suitable for dielectrophoresis and a method for concentrating particles with the same.

DETAILED DESCRIPTION OF THE EMBODIMENT

Hereinafter, the embodiment of the present invention will be described in more detail with reference to the drawings.

Figure 1A:
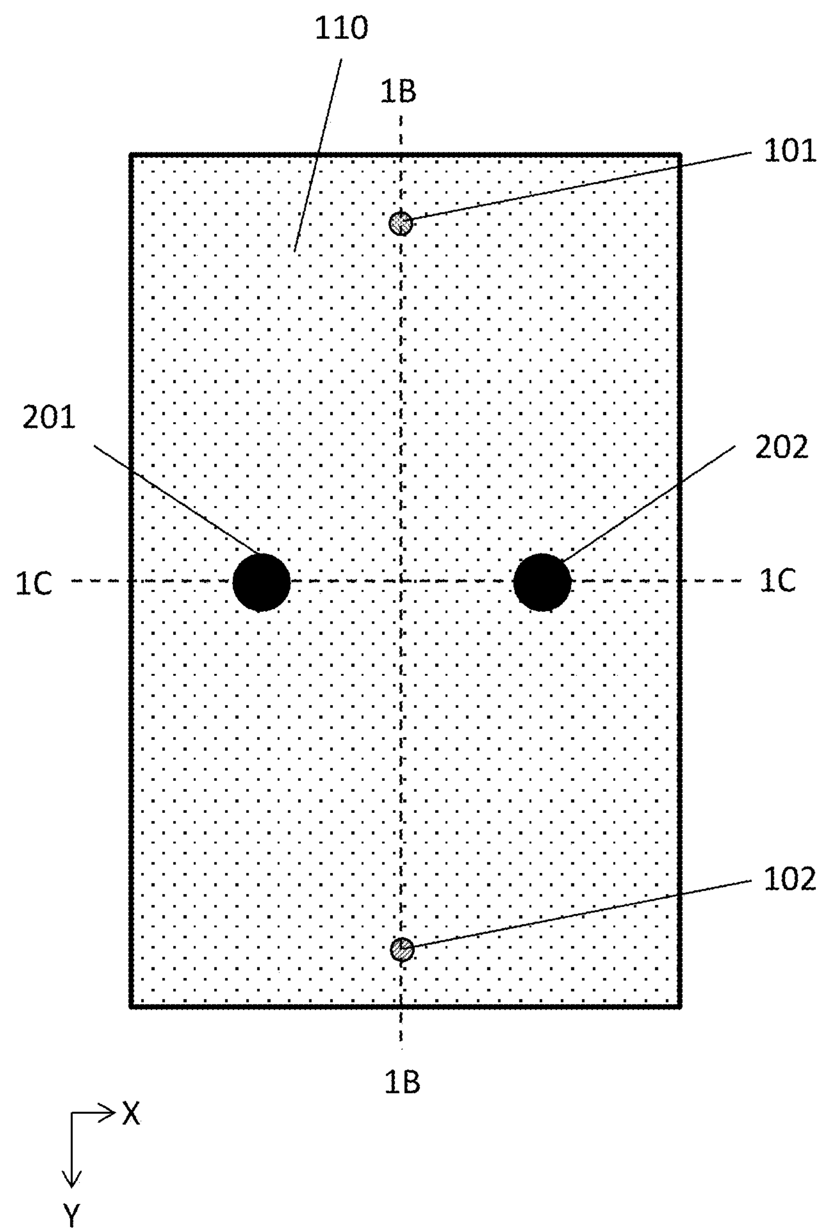
FIG. 1A shows a top view of a concentration device according to the embodiment.
Figure 1B:
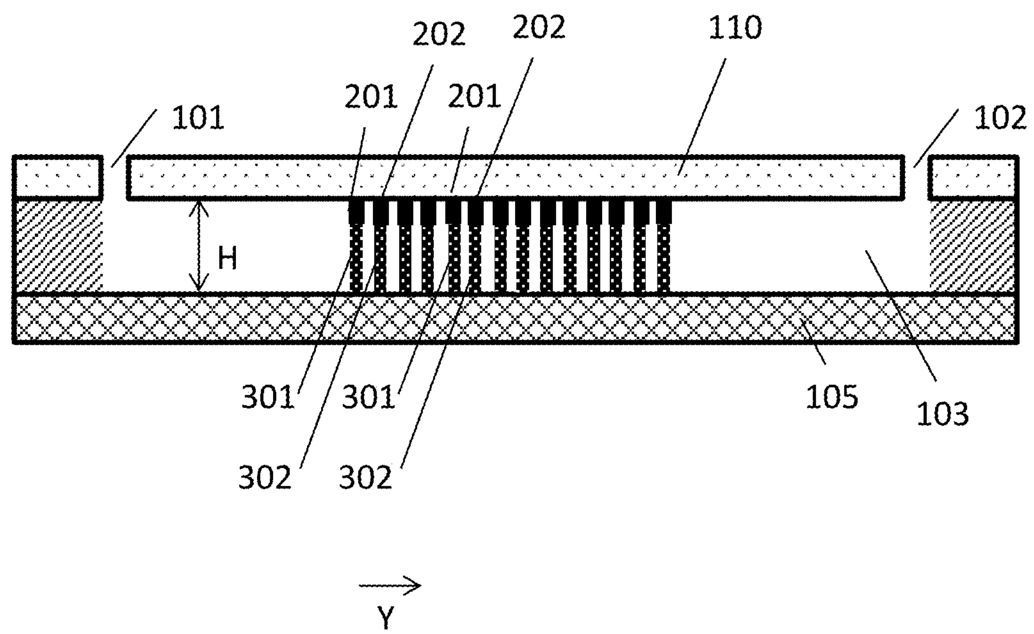
FIG. 1B shows a cross-sectional view taken along the line 1B-1B included in FIG. 1A.
Figure 1C:
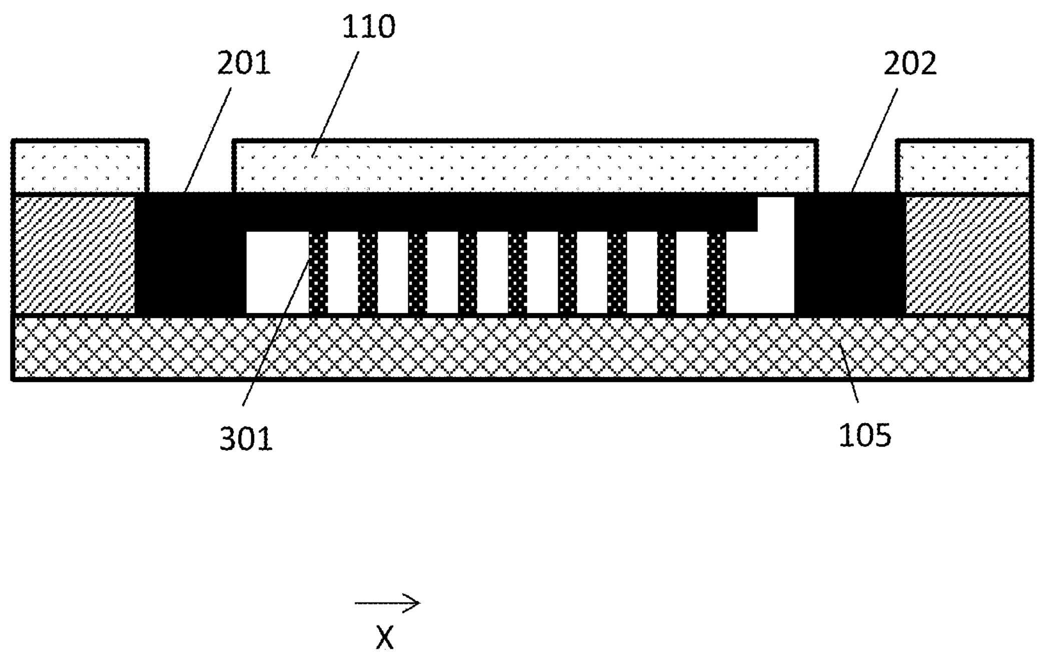
FIG. 1C shows a cross-sectional view taken along the line 1C-1C included in FIG. 1A.

FIG. 1A shows a top view of a concentration device according to the embodiment. FIG. 1B shows a cross-sectional view taken along the line 1B-1B included in FIG. 1A. FIG. 1C shows a cross-sectional view taken along the line 1C-1C included in FIG. 1A.

As shown in FIG. 1B and FIG. 1C, the concentration device according to the embodiment comprises a first substrate 110 and a second substrate 105. The second substrate 105 faces the first substrate 110. A flow path 103 is formed between the first substrate 110 and the second substrate 105. The flow path 103 has a height H and a width W.

Figure 1D:
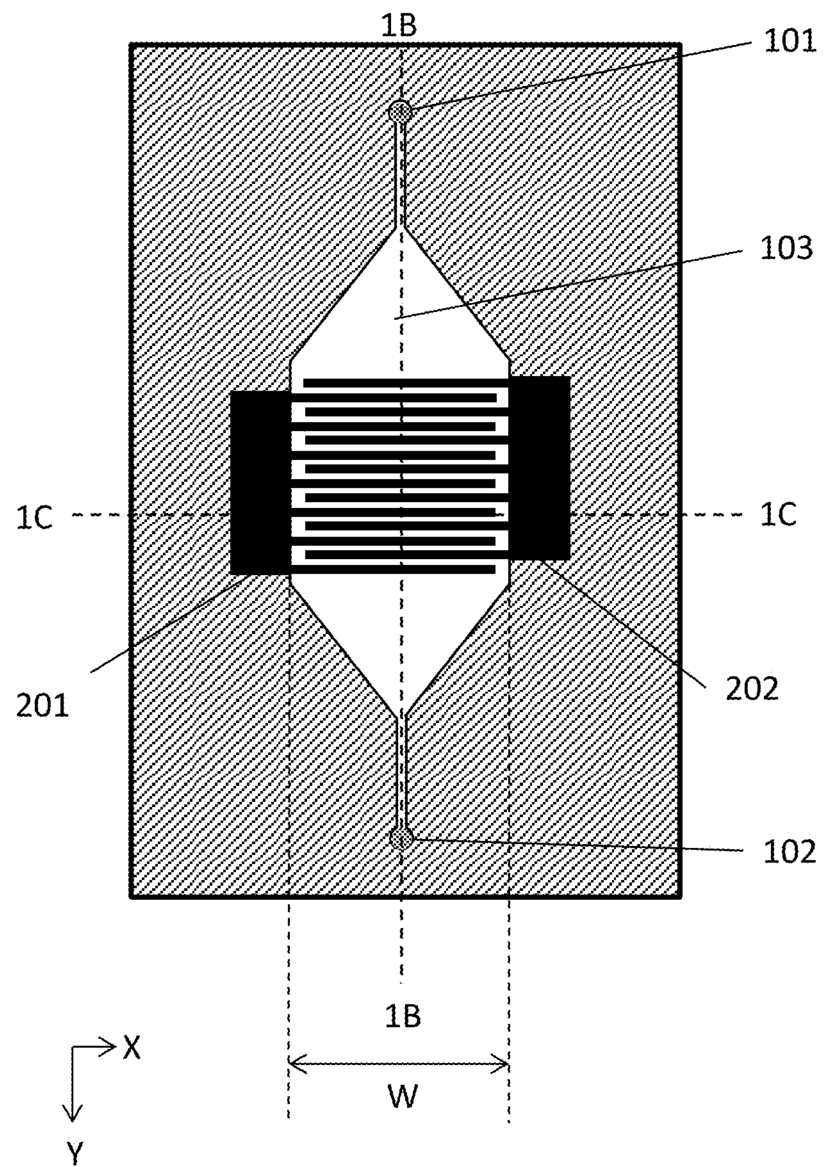
FIG. 1D shows a schematic view of a back surface of a first substrate 110.

FIG. 1D shows a schematic view of the back surface of the first substrate 110. FIG. 1A is a schematic view of the front surface of the first substrate 110. As shown in FIG. 1A-FIG. 1D, the first substrate 110 comprises an inlet 101 and an outlet 102. The inlet 101 and the outlet 102 are through-holes. The inlet 101 communicates with the outlet 102 through the flow path 103. Therefore, a samples solution is injected through the inlet 101. The thus-injected samples solution flows through the flow path 103. Finally, the samples solution is discharged from the outlet 102. As is clear from FIG. 1A-FIG. 1D, the concentration device according to the present embodiment is a chip for concentration (hereinafter, which may be referred to as a "concentration chip").

The back surface of the first substrate 110 is provided with a first comb-shaped electrode 201 and a second comb-shaped electrode 202. The first comb-shaped electrode 201 and the second comb-shaped electrode 202 engage each other.

The inside of the flow path 103 is provided with first pillar electrodes 301 and second pillar electrodes 302. The first pillar electrodes 301 are electrically connected to the first comb-shaped electrode 201. The second pillar electrodes 302 are electrically connected to the second comb-shaped electrode 202. Of course, the first pillar electrodes 301 are electrically insulated from the second comb-shaped electrode 202. Similarly, the second pillar electrodes 302 are electrically insulated from the first comb-shaped electrode 201.

Figure 2:
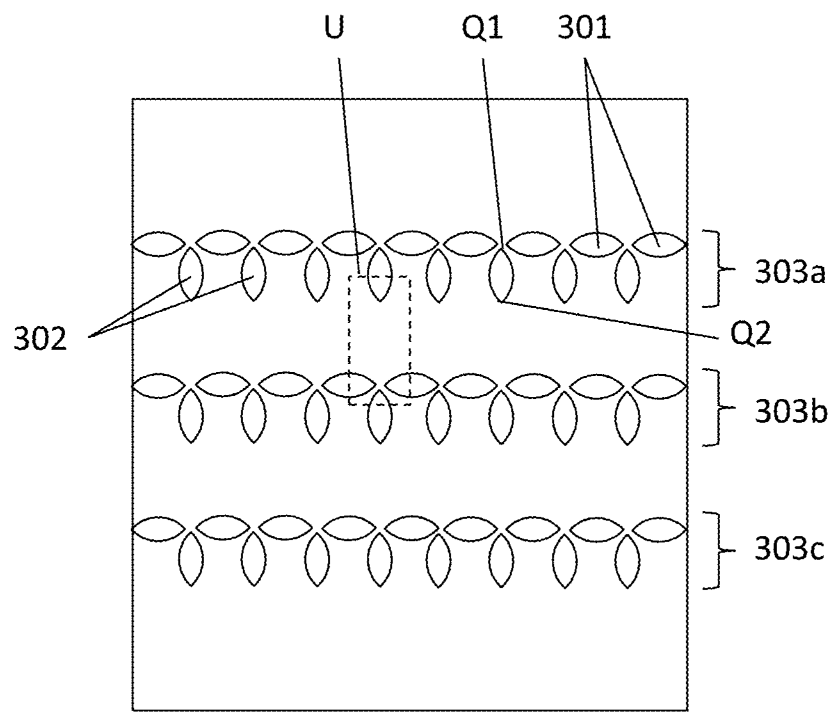
FIG. 2 shows a top view of first pillar electrodes 301 and second pillar electrodes 302.

Now, the first pillar electrodes 301 and the second pillar electrodes 302 will be described in more detail. FIG. 2 shows a top view of the first pillar electrodes 301 and the second pillar electrodes 302. When viewed in the top view, each of the first pillar electrodes 301 has a shape of a rugby ball. Each of the second pillar electrodes 302 also has a shape of a rugby ball. One pillar electrode line 303 is composed of plural first pillar electrodes 301 and plural second pillar electrodes 302. In other words, one pillar electrode line 303 includes plural first pillar electrodes 301 and plural second pillar electrodes 302. Plural pillar electrode lines 303 are formed in the flow path 103. Each of the pillar electrode lines 303 is parallel to an X-axis direction. In this way, two or more pillar electrode lines 303 are formed in the flow path 103.

Figure 3:
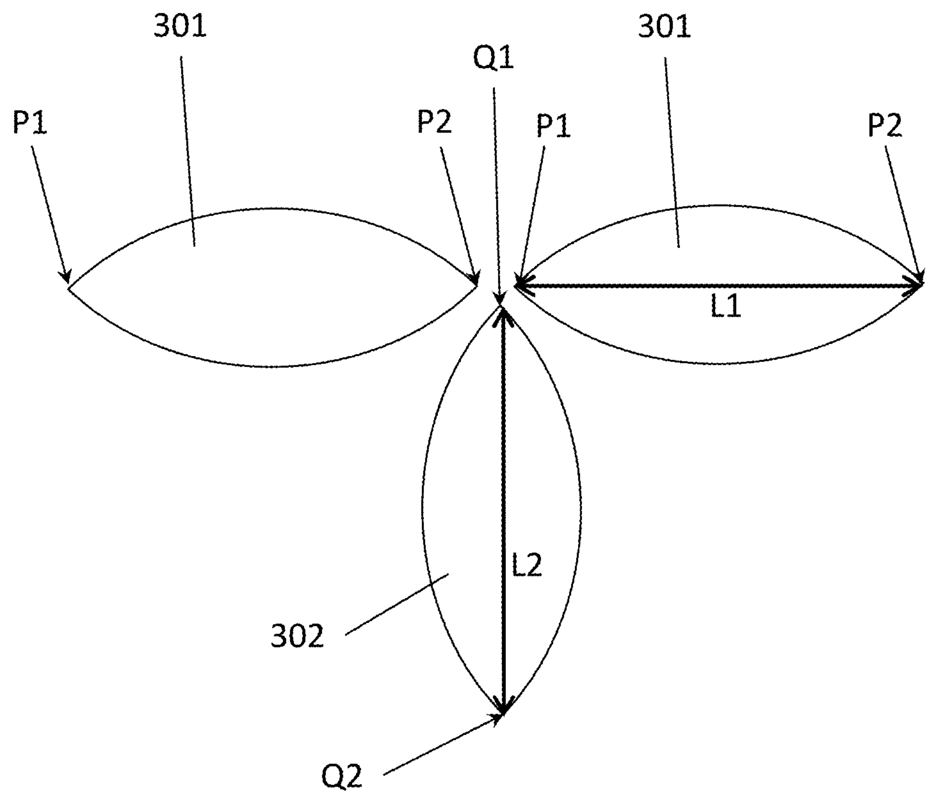
FIG. 3 shows a top view of two adjacent first pillar electrodes 301 and one second pillar electrode 302 thereby.

FIG. 3 shows a top view of two adjacent first pillar electrodes 301 and one second pillar electrode 302 thereby. Each of the first pillar electrodes 301 includes a first vertex P1 and a second vertex P2. The line segment between the first vertex P1 and the second vertex P2 included in each of the first pillar electrodes 301 has a length L1 in the X-axis direction. Each of the second pillar electrodes 302 includes a first vertex Q1 and a second vertex Q2. The line segment between the first vertex Q1 and the second vertex Q2 included in each of the second pillar electrodes 302 has a length L2 in the Y-axis direction. The first vertex Q1 is near the first vertex P1 and the second vertex P2. On the other hand, the second vertex Q2 is far from the first vertex P1 and the second vertex P2. In other words, as shown in FIG. 2, the second vertex Q2 included in the second pillar electrode 302 included in the first pillar electrode line 303*a* is closer to the second pillar electrode line 302*b* than the first vertex Q1 included in the second pillar electrodes 302 included in the first pillar electrode line 303*a*. A third pillar electrode line 303*c* may be provided. Needless to say, the X-axis direction is perpendicular to the Y-axis direction.

Figure 4:
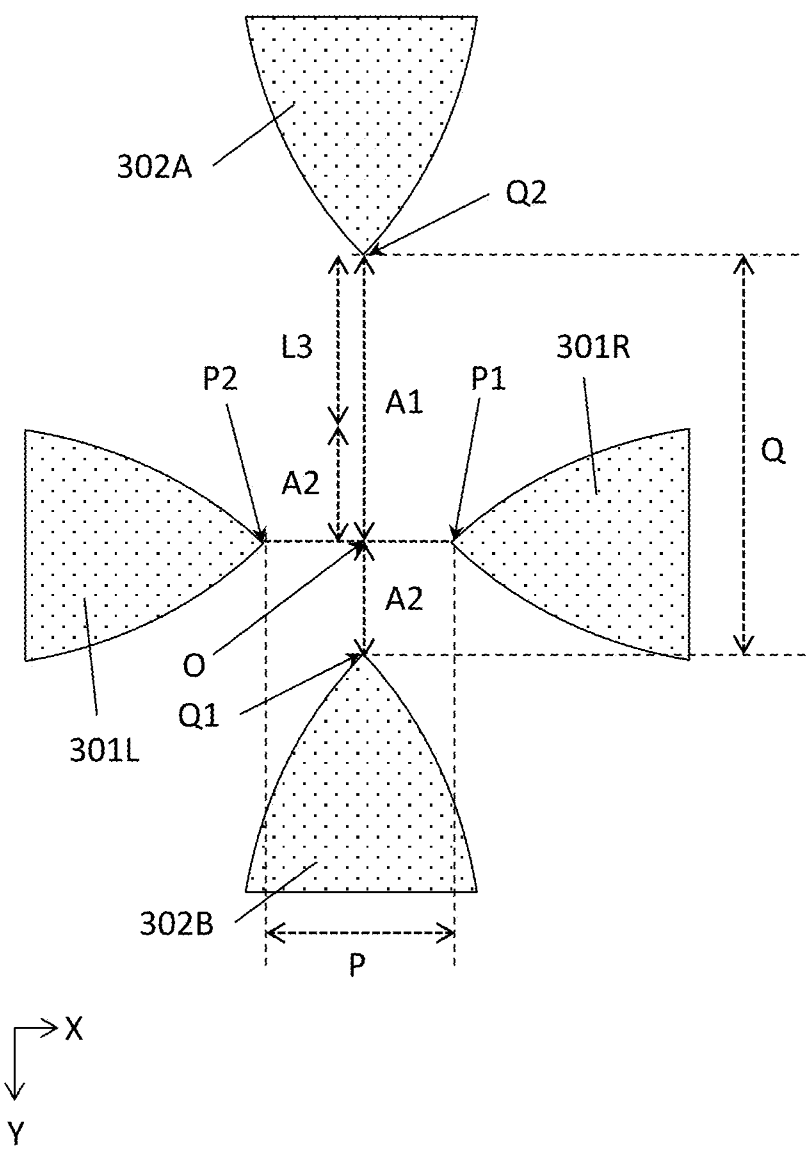
FIG. 4 shows a top view of the two first pillar electrodes 301 and the two second pillar electrodes 302.

FIG. 4 shows an enlarged view of a region U surrounded by a dot line included in FIG. 2. FIG. 4 is a drawing showing one pillar electrode group included in the region U. As shown in FIG. 4, the one pillar electrode group is composed of the following four electrodes (I)-(IV):

(I) one left-side first pillar electrode 301L selected from the first pillar electrodes 301 included in the second pillar electrode line 303*b;*

(II) one right-side first pillar electrode 301R selected from the first pillar electrodes 301 included in the second pillar electrode line 303*b;*

(III) one second pillar electrode 302A selected from the second pillar electrodes 302 included in the first pillar electrode 303*a*; and (IV) one second pillar electrode 302B selected from the second pillar electrodes 302 included in the second pillar electrode 303*b*.

The left-side first pillar electrode 301L and the right-side first pillar electrode 301R are adjacent to each other in such a manner that the second vertex P2 of the left-side first pillar electrode 301L and the first vertex P1 of the right-side first pillar electrode 301R face each other.

As is clear from FIG. 4, a line which passes through the second vertex P2 of the left-side first pillar electrode 301L and the first vertex P1 of the right-side first pillar electrode 301R is parallel to the X-axis direction.

A line which passes through the second vertex Q2 of the second pillar electrode A and the first vertex Q1 of the second pillar electrode B is parallel to the Y-axis direction.

As shown in FIG. 4, the center point O, the line segment P, and the line segment Q are defined as below.

The center point O is an intersection point of the line segment P and the line segment Q. The four electrodes included in the one pillar electrode group surround the center point O in the top view.

The line segment Q is a line segment between the second vertex Q2 of the second pillar electrode 302A and the first vertex Q1 of the second pillar electrode 302B.

The line segment P is a line segment between the second vertex P2 of the left-side first pillar electrode 301L and the first vertex P1 of the right-side first pillar electrode 301R.

The present embodiment is characterized by that the following mathematical formula (I) is satisfied.

$$L3 \geq 5 \text{ micrometers} \tag{I}$$

where $$L3 = A1 - A2,$$

A1 represents a distance between the second vertex Q2 of the second pillar electrode 302A and the center point O; and A2 represents a distance between the first vertex Q1 of the second pillar electrode 302B and the center point O.

In the present embodiment, since the value of L3 is not less than 5 micrometers, as demonstrated in the simulation examples B1-B7, dielectrophoresis force is given as attractive force to particles flowing through the center point O. For this reason, the particles are captured only at and around the center point O against the stream of the fluid (i.e., the sample solution) flowing through the flow path 103. In this way, the particles are concentrated at and around the center point O. In case where the value of L3 is 0 micrometers, as demonstrated in the simulation examples B1-B7, dielectrophoresis force is given as repulsive force to the particles flowing through the center point O. For this reason, the repulsive force accelerates the stream of the particles flowing through the flow path 103. Consequently, the particles fail to be captured. The particles flow faster toward the lower course of the flow path 103.

As demonstrated in the simulation examples B1-B4, it is desirable that the value of L3 is not less than 5 micrometers. See FIG. 17-FIG. 20.

As demonstrated in the simulation example B5, it is desirable that the value of A2 is not more than 2.8 micrometers. See FIG. 21.

As demonstrated in the simulation example B6, it is desirable that the length of the line segment P is not more than 5.6 micrometers. See FIG. 22.

(Fabrication Method)

Hereinafter, a method for fabricating the concentration devices according to the embodiment will be described with reference to FIG. 24A-FIG. 24F. The concentration device according to the embodiment may be fabricated using a common fabrication method of semiconductor devices.

Figure 24A:
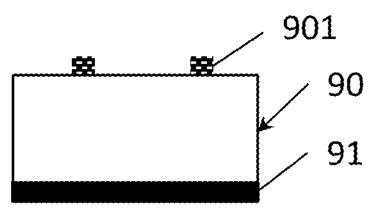
FIG. 24A shows a cross-sectional view of a silicon substrate 90 in one step included in a method for fabricating a concentration device according to the embodiment.

First, as shown in FIG. 24A, a first resist 901 is patterned on an upper surface of a silicon substrate 90 comprising an insulating layer 91 at the bottom surface thereof. Then, as shown in FIG. 24B, a second resist 902 is further patterned. Subsequently, as shown in FIG. 24C, a part of the silicon substrate 90 on which neither the first resist 901 nor the second resist 902 is formed is etched using both of the first resist 901 and the second resist 902 as a mask. A bottom of the etched part is located in the inside of the silicon substrate 90.

Figure 24D:
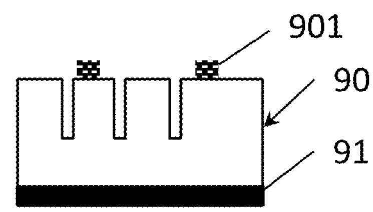
FIG. 24D shows a cross-sectional view of the silicon substrate 90 in one step, subsequent to FIG. 24C, included in the method.
Figure 24B:
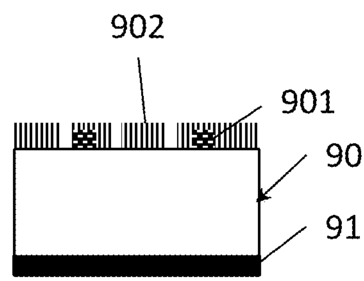
FIG. 24B shows a cross-sectional view of the silicon substrate 90 in one step, subsequent to FIG. 24A, included in the method.
Figure 24E:
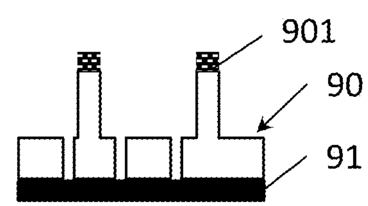
FIG. 24E shows a cross-sectional view of the silicon substrate 90 in one step, subsequent to FIG. 24D, included in the method.
Figure 24C:
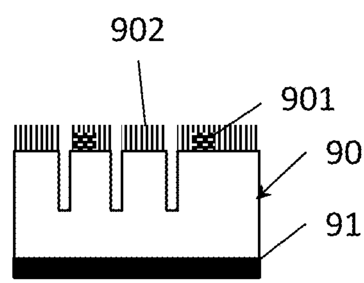
FIG. 24C shows a cross-sectional view of the silicon substrate 90 in one step, subsequent to FIG. 24B, included in the method.
Figure 24F:
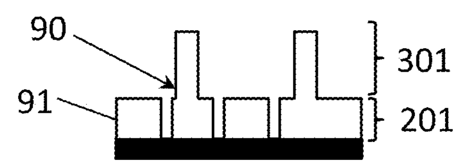
FIG. 24F shows a cross-sectional view of the silicon substrate 90 in one step, subsequent to FIG. 24E, included in the method.
Figure 25:
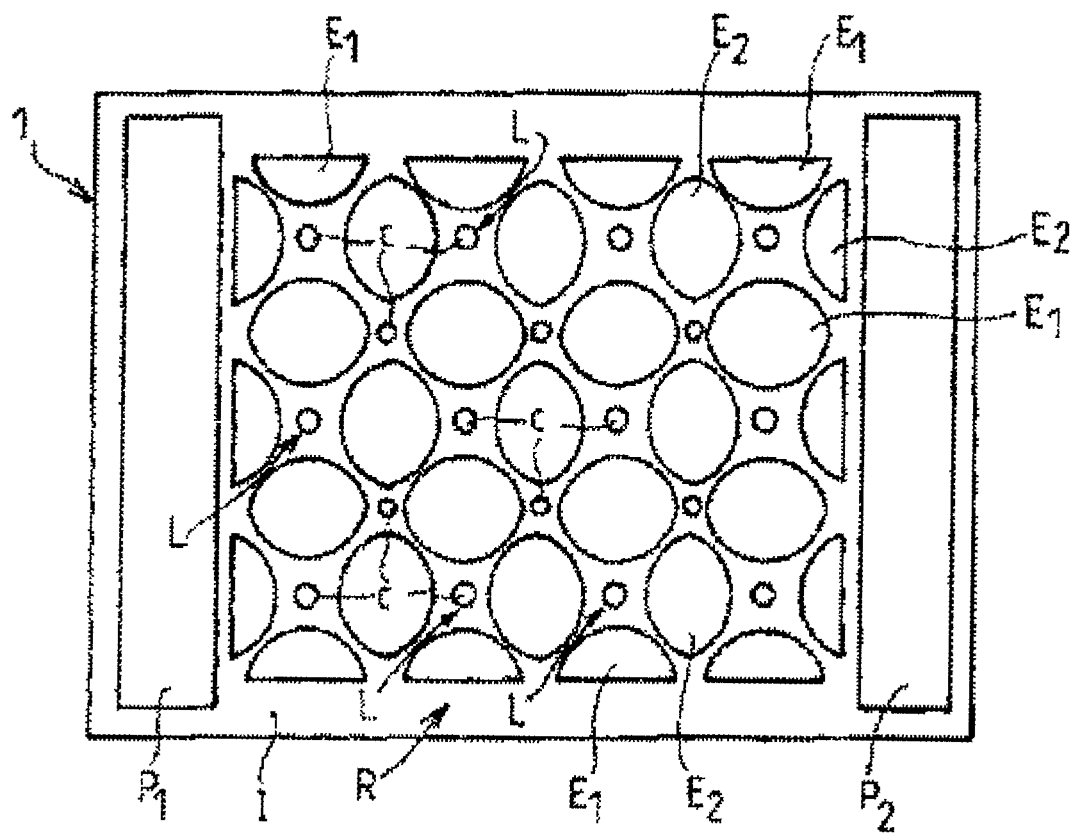
FIG. 25 is a duplicate of FIG. 1 included in Patent Literature 1.

As shown in FIG. 24D, the second resist 902 is removed. Then, as shown in FIG. 24E, the silicon substrate 90 is etched using the first resist 901 as a mask. The bottom of the etched part reaches a front surface of the insulating layer 91. At this stage, the flow path 103 having the height H and the width W is formed. Finally, the first resist 901 is removed as shown in FIG. 24F. In this way, the first substrate 110 is formed. After the inlet 101 and the outlet 102 are formed, the first substrate 110 is joined onto the second substrate 105.

(Concentration Method)

Hereinafter, a method for concentrating particles contained in a sample solution using a concentration device according to the embodiment will be described. In the present embodiment, each of the particles has a diameter of not less than 30 nanometers and not more than 100 nanometers. An example of the particle is influenza virus (particle size: approximately 100 nanometers) or norovirus (particle size: approximately 30 nanometers).

First, the concentration device according to the embodiment is prepared. Specifically, a user of the concentration device purchases the concentration device according to the embodiment from the present patentee or its licensee.

Then, the sample solution is supplied between the first substrate 110 and the second substrate 105. Specifically, the sample solution is injected through the inlet 101. The injected sample solution flows through the flow path 103.

While the sample solution flows through the flow path 103, an alternating voltage is applied between the first pillar electrodes 301 and the second pillar electrodes 302 through the first comb-shaped electrode 201 and the second comb-shaped electrode 202. Desirably, the applied alternating voltage has a voltage of not less than 5 volts pp and not more than 20 volts pp and a frequency of not less than 50 kilohertz and not more than 20 megahertz. The term "pp" means peak-to-peak.

This alternating voltage forms a region having a significantly high electric field at and around the center point O. This high electric field gives dielectrophoresis force as the attractive force at and around the center point O. Due to this dielectrophoresis force as the attractive force, the particles are captured only at and around the center point O against the stream of the fluid (namely, the sample solution) flowing through the flow path 103. In other words, the dielectrophoresis force as attractive force is greater than force given to the particles by the sample solution flowing through the flow path 103 along the +Y direction. In this way, the particles are concentrated center only at and around the center point O. Finally, the sample solution is discharged from the outlet 102, whereas the particles are left at and around the center point O.

As above described, the value of L3 is not less than 5 micrometers. In case where the value of L3 is 0 micrometers, as demonstrated in the simulation examples B1-B7, dielectrophoresis as the repulsive force given to the particles accelerates the stream of the particles. For this reason, the particles are not captured and flow faster toward the lower course of the flow path 103 (namely, in the +Y direction).

The word "parallel" used in the instant specification may include an angular error of not more than 5 degrees. Likewise, the word "perpendicular" may include an angular error of not more than 5 degrees.

EXAMPLES

Hereinafter, the present invention will be described in more detail with reference to the following examples.

Inventive Example 1

In the inventive example 1, a sample solution containing fluorescence polystyrene particles was used. The sample solution was prepared by diluting fluorescence polystyrene particles (available from Polysciences company, trade name: Fluoresbrite Yellow Green Carboxylate Microspheres, particle size: 0.1 micrometer, w/v concentration: 2.6%) 100,000 fold with a 1% Tween20 aqueous solution. The sample solution had fluorescence polystyrene particle concentration of approximately $4.7\times10^{8}$ $ml^{-1}$.

A SOI substrate was etched as shown in FIG. 24A-FIG. 24F to fabricate a first substrate 110. The first substrate 110 was joined onto a second substrate 105. In this way, a concentration device according to the inventive example 1 was fabricated.

The following table 1 shows the details of the concentration device according to the inventive example 1.

TABLE 1

| | |
|---|---|
| Number of Pillar Electrode Lines 303 | 26 |
| Number of First Pillar Electrodes 301 in each pillar electrode line 303 | 26 |
| Number of Second Pillar Electrodes 302 in each pillar electrode line 303 | 35 |
| L1 | 25.5 micrometers |
| L2 | 25.5 micrometers |
| P | 2.8 micrometers |
| Q | 31.1 micrometers |
| A1 | 29.7 micrometers |
| A2 | 1.4 micrometers |
| L3 | 28.3 micrometers |
| H | 50 micrometers |
| W | 1,000 micrometers |

Then, ethanol was supplied at a flow rate of 20 microliters/minute through an inlet 101 for five minutes. In this way, air was removed from the flow path 103. Furthermore, 1% Tween20 aqueous solution was supplied at a flow rate of 20 microliters/minute through the inlet 101 for five minutes. In this way, the ethanol was removed from the flow path 103. The flow path 103 was filled with 1% Tween20 aqueous solution.

Figure 5:
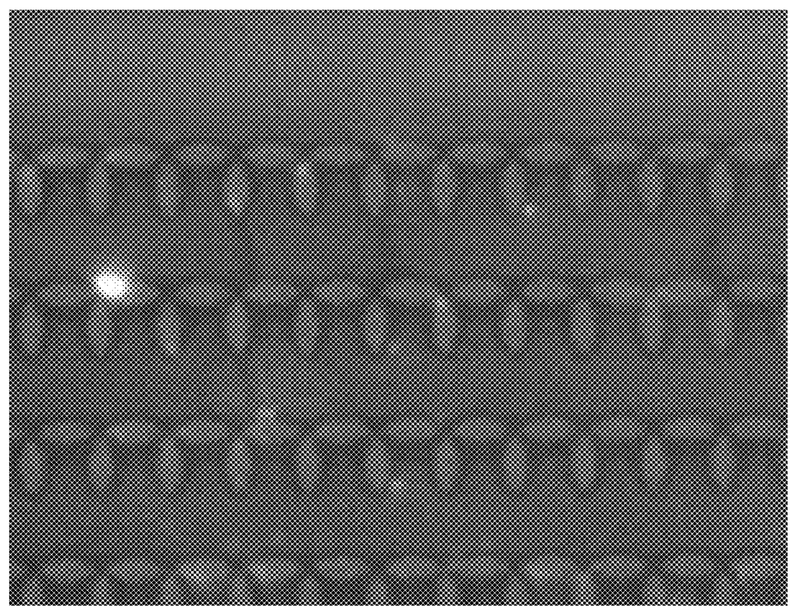
FIG. 5 is a fluorescent microscope photograph of a flow path 103 through which a sample solution flows without applying an alternating voltage in the inventive example 1.

Then, a sample solution was supplied at a flow rate of 20 microliters/minute through the inlet 101 for five minutes. FIG. 5 is a fluorescent microscope photograph of the flow path 103 through which the sample solution flowed. At this stage, an alternating voltage was not applied.

Figure 6:
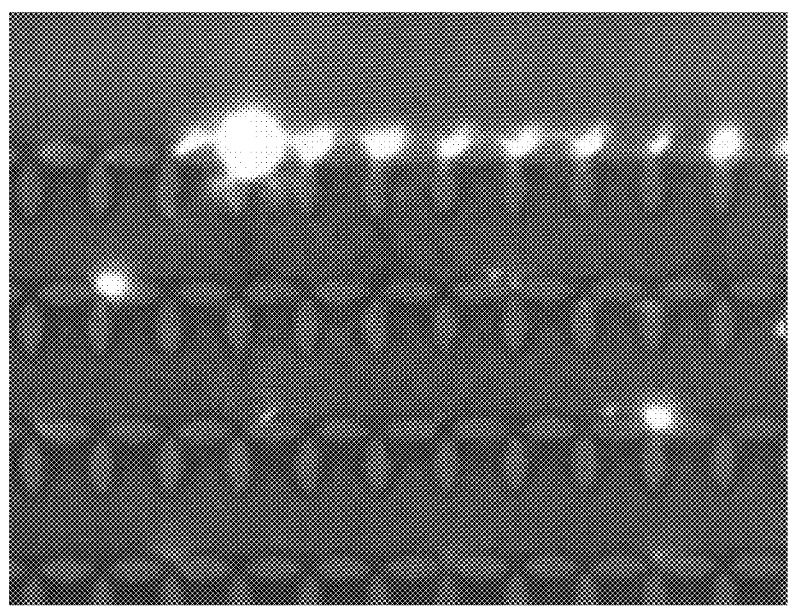
FIG. 6 is a fluorescent microscope photograph of the flow path 103 through which the sample solution flows while an alternating voltage is applied in the inventive example 1.

The supply of the sample solution was continued, while an alternating voltage having a voltage of 14.14 volts pp and a frequency of 5 MHz between the first pillar electrodes 301 and the second pillar electrodes 302 was applied through the first comb-shaped electrode 201 and the second comb-shaped electrode 202. FIG. 6 is a fluorescent microscope photograph of the flow path 103 through which the sample solution flowed while the alternating voltage was applied.

Figure 7:
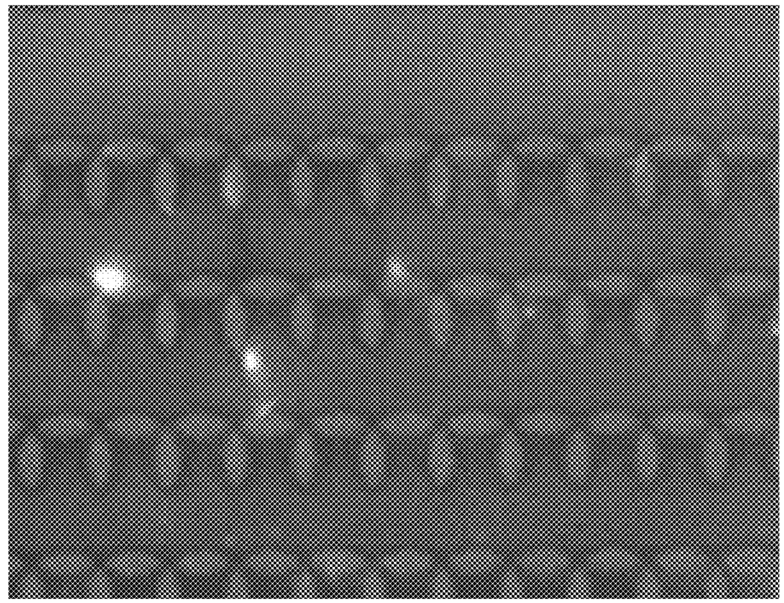
FIG. 7 is a fluorescent microscope photograph of the flow path 103 after five seconds of an end of the application of the alternating voltage in the inventive example 1.

Finally, the application of the alternating voltage was stopped. The supply of the sample solution was continued. FIG. 7 is a fluorescent microscope photograph of the flow path 103 after five seconds of an end of the application of the alternating voltage.

As is clear from FIG. 5-FIG. 7, even if the supply of the sample solution is continued, the particles are concentrated at and around the center point O during the application of the alternating voltage.

Inventive Example 2

Figure 8:
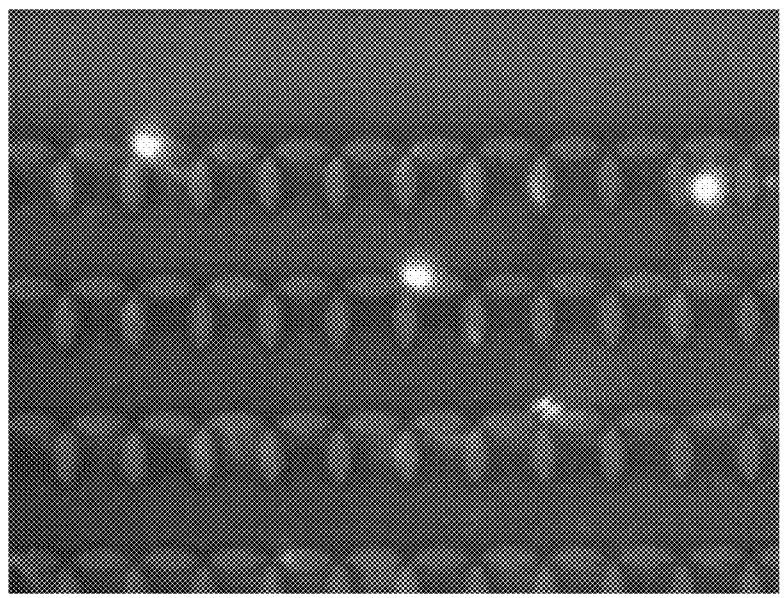
FIG. 8 is a fluorescent microscope photograph of the flow path 103 through which a sample solution flows without applying an alternating voltage in the inventive example 2.
Figure 9:
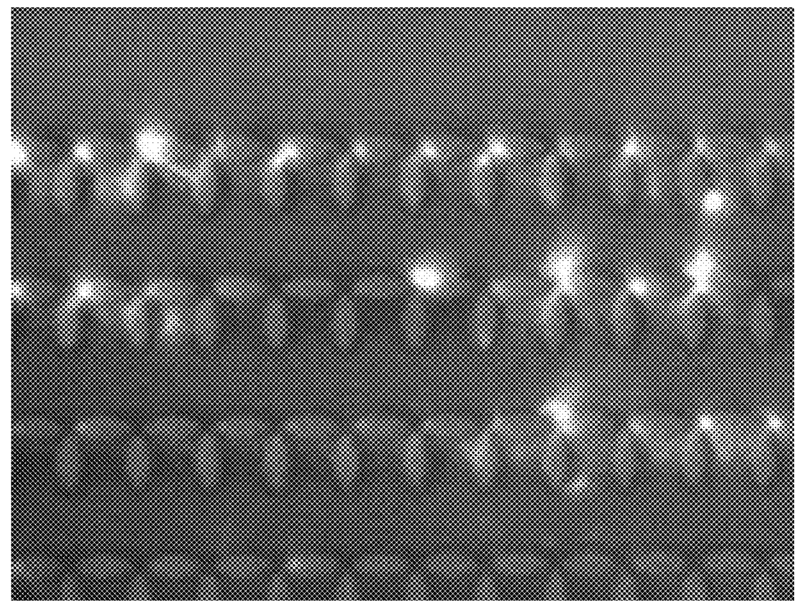
FIG. 9 is a fluorescent microscope photograph of the flow path 103 through which the sample solution flows while an alternating voltage is applied in the inventive example 2.
Figure 10:
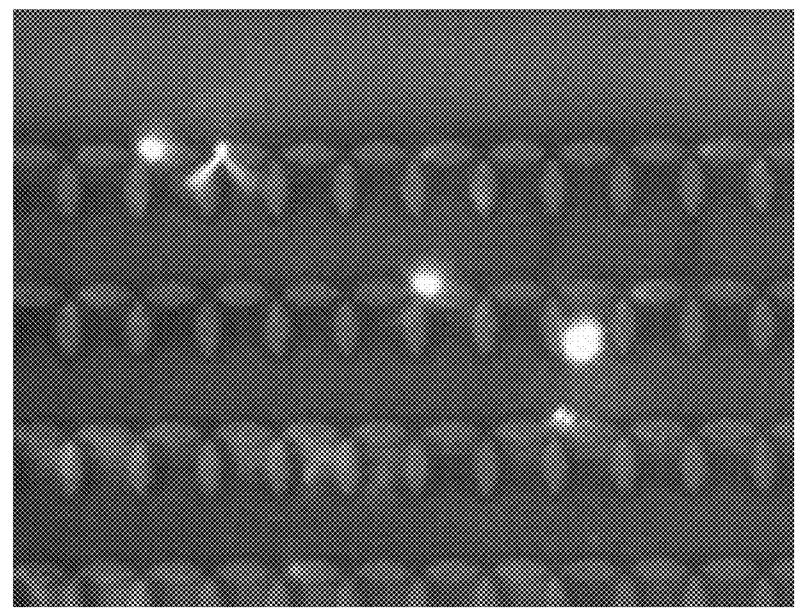
FIG. 10 is a fluorescent microscope photograph of the flow path 103 after five seconds of an end of the application of the alternating voltage in the inventive example 2.

In the inventive example 2, an experiment similar to the inventive example 1 was conducted, except that the alternating voltage had a voltage of 7 volts pp and a frequency of 100 kilohertz. FIG. 8-FIG. 10 are fluorescent microscope photographs which correspond to FIG. 5-FIG. 7 respectively. As is clear from FIG. 8-FIG. 10, also in the inventive example 2, even if the supply of the sample solution is continued, the particles are concentrated at and around the center point O during the application of the alternating voltage.

Inventive Example 3

Figure 11:
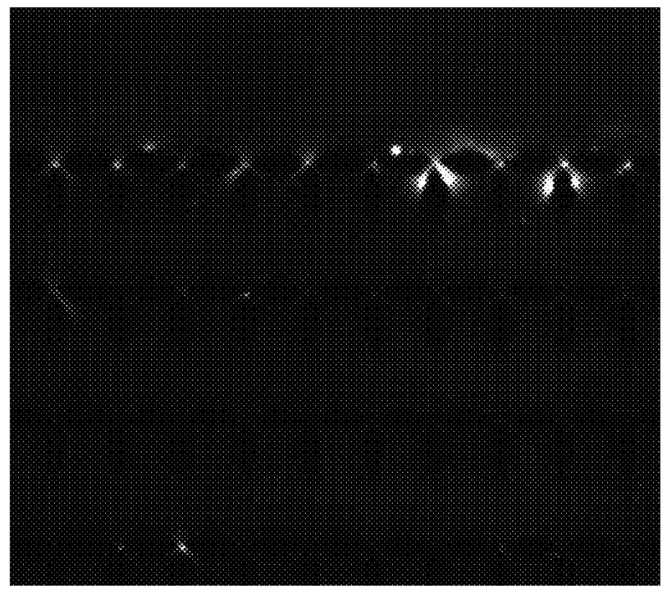
FIG. 11 is a fluorescent microscope photograph taken before an application of an alternating voltage in the inventive example 3.
Figure 12:
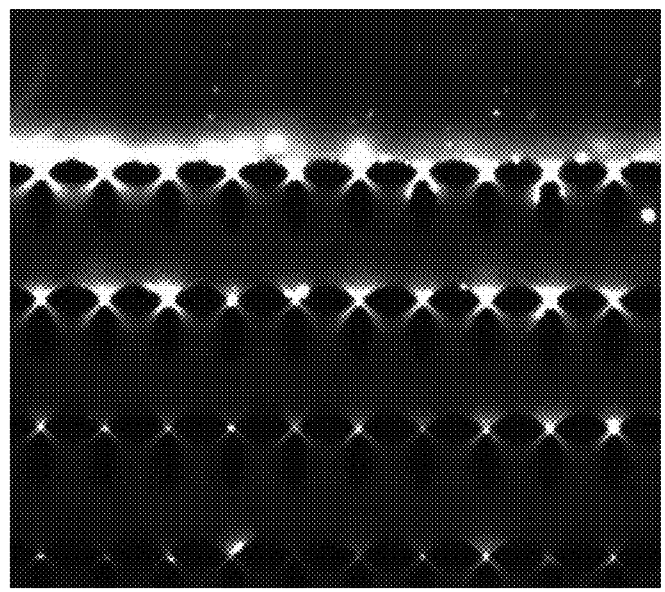
FIG. 12 is a fluorescent microscope photograph taken during an application of the alternating voltage in the inventive example 3.

In the inventive example 3, an experiment similar to the inventive example 1 was conducted, except that the sample solution contained not fluorescence polystyrene particles but inactivated influenza virus particles and that the alternating voltage had a voltage of 10 volts pp and a frequency of 500 kilohertz. FIG. 11 is a fluorescent microscope photograph taken before an application of an alternating voltage. FIG. 12 is a fluorescent microscope photograph taken during the application of the alternating voltage. In both of FIG. 11 and FIG. 12, the supply of the sample solution was continued. As is clear from FIG. 11 and FIG. 12, also in the inventive example 3, even if the supply of the sample solution is continued, the influenza virus particles are concentrated at and around the center point O during the application of the alternating voltage.

The sample solution containing the inactivated influenza virus particles was prepared as below. The influenza virus was H1N1 type A/Hyogo/YS/2011 strain contained in allantoic fluid of a chicken egg cultured in Graduate School of Veterinary Medicine, Hokkaido University. The influenza virus was inactivated using β-propiolactone.

Then, the inactivated influenza virus was dyed as below. Fluorescent dye (from Biotium company, trade name: 30022 CellBriteOrange Cyvertexlasmic Membrane Dye 1 ml Dil cell labeling solution, 5 microliters) was diluted with 500 milliliters of saline. Soon after that, the saline containing the fluorescent dye is mixed with the aqueous solution of the inactivated influenza virus (500 milliliters). In this way, a mixture solution was obtained. The mixture solution was left at rest 37 degrees Celsius for 20 minutes. In this way, the inactivated influenza virus was dyed.

A mannitol aqueous solution (concentration: 280 mM, volume: 1 milliliter) was added to the aqueous solution of the inactivating influenza virus. The aqueous solution was filtered with a filter of 0.45 micrometers. In this way, impurities each having a diameter of not less than 0.45 micrometers were removed. Then, the aqueous solution was condensed with a centrifugal filter having filtration accuracy of the 100 kDa molecular weight so as to have a volume of approximately 60 microliters. Finally, a mannitol aqueous solution (concentration: 280 mM, volume: 600 microliters) was added so that the aqueous solution had electrical conductivity of 0.78 mS/cm. In this way, the sample solution containing the inactivating influenza virus was prepared.

Simulation Example A1

In the simulation example A1, the concentration of the particles was simulated under a condition shown in the following Table 2 using a simulator (available from COMSOL company, trade name: COMSOL Multiphysics).

TABLE 2

| | |
|---|---|
| Number of Pillar Electrode Line 303 | 3 |
| Number of First Pillar Electrodes 301 in each pillar electrode line 303 | 10 |
| Number of Second Pillar Electrodes 302 in each pillar electrode line 303 | 10 |
| L1 | 25.5 micrometers |
| L2 | 25.5 micrometers |
| P | 2.8 micrometers |
| Q | 31.1 micrometers |
| A1 | 29.7 micrometers |
| A2 | 1.4 micrometers |
| L3 | 28.3 micrometers |
| H | 50 micrometers |
| W | 280 micrometers |
| Top-view shape of First Pillar Electrode 301 | Rugby ball |
| Top-view shape of Second Pillar Electrode 302 | Rugby ball |
| Voltage | 10 volts pp |

Figure 13:
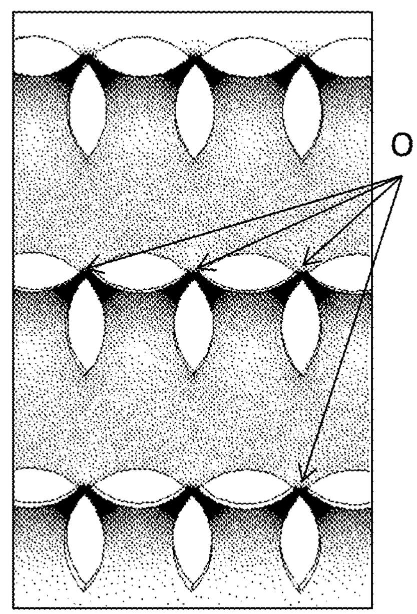
FIG. 13 is a top view of the simulation result in the simulation example A1.

FIG. 13 is a top view showing the simulation results in the simulation example A1. An electric field increases with an increase in the density of black dots. As is clear from FIG. 13, a region having a significantly high electric field is formed at and around the center point O.

Simulation Example A2

Figure 14:
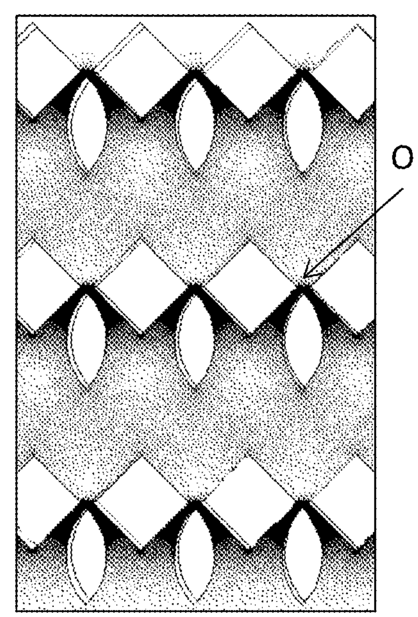
FIG. 14 is a top view of the simulation result in the simulation example A2.

In the simulation example A2, the simulation similar to the simulation example A1 was conducted, except that each of the first pillar electrodes 301 had a shape of a lozenge and a square in a top view. FIG. 14 is a top view showing the simulation results in the simulation example A2. As is clear from FIG. 14, a region having a significantly high electric field is formed at and around the center point O.

Simulation Example A3

Figure 15:
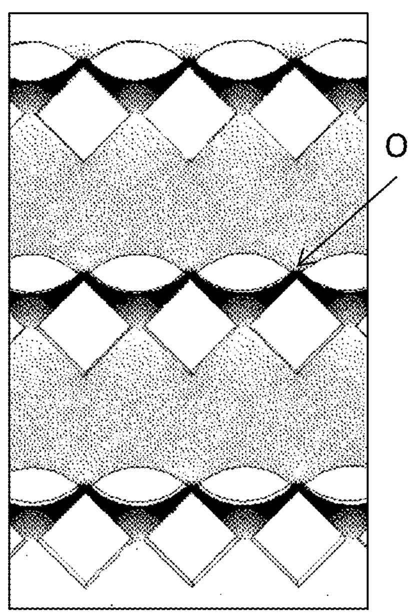
FIG. 15 is a top view of the simulation result in the simulation example A3.

In the simulation example A3, the simulation similar to the simulation example A1 was conducted, except that each of the second pillar electrodes 302 had a shape of a lozenge and a square in a top view. FIG. 15 is a top view showing the simulation results in the simulation example A3. As is clear from FIG. 15, a region having a significantly high electric field is formed at and around the center point O.

As is clear from FIG. 13-FIG. 15, the top-view shape of the first pillar electrodes 301 and the second pillar electrodes 302 is not limited, as far as the following four requirements (I)-(IV) are satisfied.

(I) Each of the first pillar electrodes 301 includes the first vertex P1 and the second vertex P2.

(II) Each of the second pillar electrodes 302 includes the first vertex Q1 and the second vertex Q2.

(III) The line segment between the first vertex P1 and the second vertex P2 is parallel to the X-axis direction.

(IV) The line segment between the first vertex Q1 and the second vertex Q2 is parallel to the Y-axis direction.

Simulation Example B1

In simulation example B1, the dielectrophoresis force given to the particles was simulated under a condition shown in the following Table 3.

TABLE 3

| | |
|---|---|
| Number of Pillar Electrode Lines 303 | 3 |
| Number of First Pillar Electrodes 301 in each pillar electrode line 303 | 10 |
| Number of Second Pillar Electrodes 302 in each pillar electrode line 303 | 10 |
| L1 | 25.5 micrometers |
| L2 | 25.5 micrometers |
| P | 2.8 micrometers |
| Q | 31.1 micrometers |
| A1 | 29.7 micrometers |
| A2 | 1.4 micrometers |
| L3 | 28.3 micrometers, 5 micrometers, or 0 micrometers |
| H | 50 micrometers |
| W | 280 micrometers |
| Top-view shape of First Pillar Electrode 301 | Rugby ball |
| Top-view shape of Second Pillar Electrode 302 | Rugby ball |
| Particle size of the particle | 100 nanometers |
| Voltage | 10 volts pp |

Figure 16:
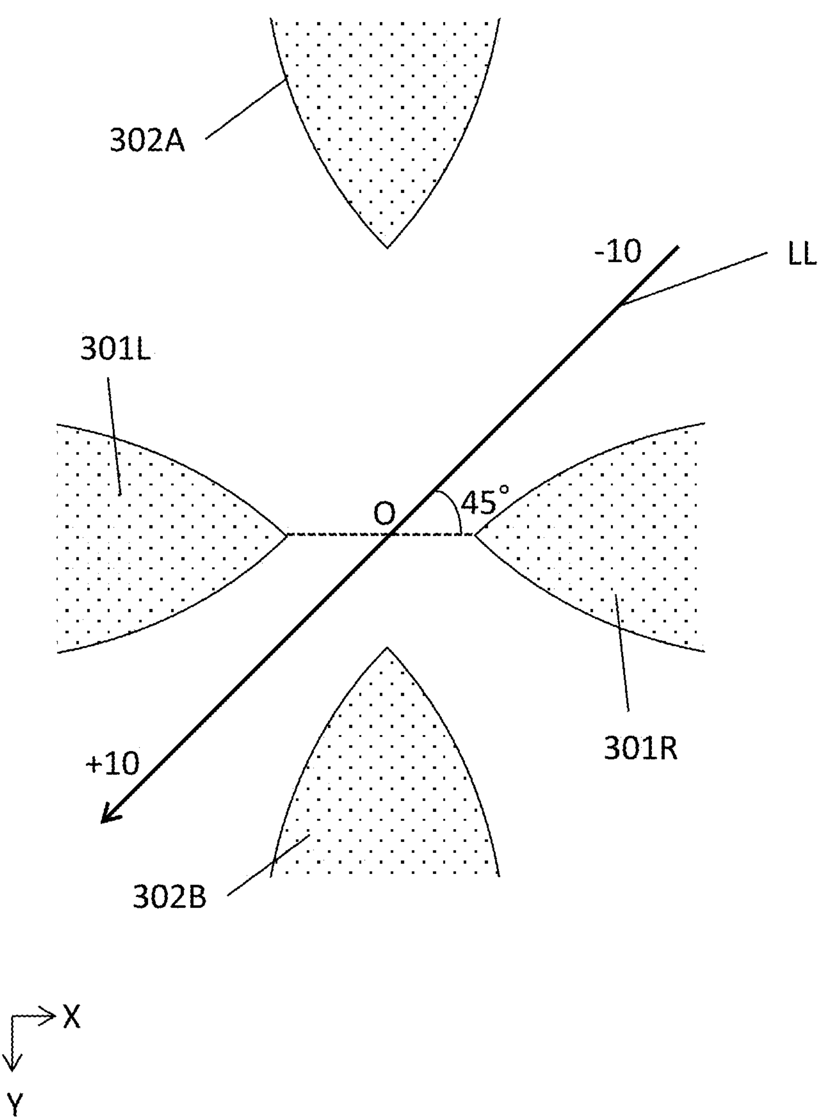
FIG. 16 shows a top view of the two first pillar electrodes 301 and the two second pillar electrodes 302.

In the simulation example B1, as shown in FIG. 16, simulated was the dielectrophoresis force given to the particle located on the straight line LL which passes through the center point O and inclines at an angle of 45 degrees with regard to the line segment P. As shown in FIG. 16, when the particle is located in the +X−Y direction from the center point O, the distance between the particle and the center point O is defined as a negative value. On the other hand, when the particle is located in the −X+Y direction from the center point O, the distance between the particle and the center point O is defined as a positive value. Needless to say, the direction in which the sample solution flows through the flow path 103 is the +Y direction.

Figures 17, 18:
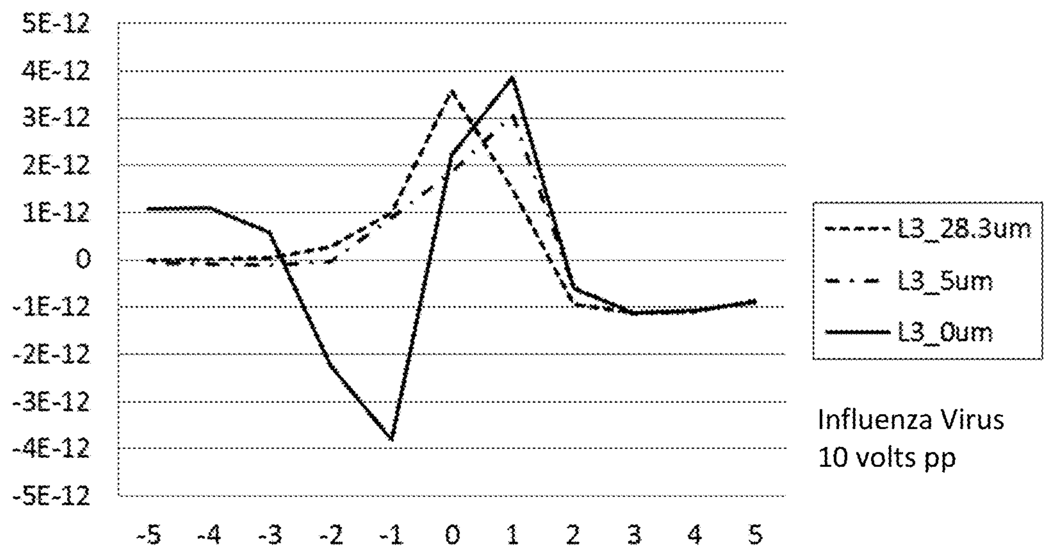
FIG. 17 is a graph showing the simulation results in the example B1.
FIG. 18 is a graph showing the simulation results in the example B2.

FIG. 17 is a graph showing the results of the simulation example B1. In the graph shown in FIG. 17, the horizontal axis represents the distance between the center point O and the particle located on the straight line LL. The vertical axis represents the dielectrophoresis force given to the particle. The positive value represents dielectrophoresis force as attractive force. The negative value represents dielectrophoresis force as repulsive force. In other words, the attractive force is given to the particle to draw the particle to the center point O in the upper region of the graph shown in FIG. 17. On the other hand, the repulsive force is given to the particle to keep the particle away from the center point O in the +Y direction in the lower region of the graph shown in FIG. 17.

As is clear from FIG. 17, if the value of L3 is not less than 5 micrometers, dielectrophoresis force is given to the particles as attractive force. Due to dielectrophoresis force as attractive force, the particles are captured only at and around the center point O against the stream of the fluid (namely, the sample solution) flowing through the flow path 103. In this way, the particles are concentrated only at and around the center point O.

On the other hand, if the value of L3 is 0 micrometers, dielectrophoresis force is given as repulsive force to the particles, while the particles approaches the center point O along the stream of the fluid (namely, the sample solution) flowing through the flow path 103. The dielectrophoresis force given as repulsive force accelerates the speed of the particles. For this reason, the particles fail to be captured and flow toward the lower course of the flow path 103. Therefore, the particles fail to be concentrated.

Simulation Example B2

In the simulation example B2, a simulation similar to the simulation example B1 was carried out, except that the diameter of the particle was 30 nanometers. FIG. 18 is a graph showing the results of the simulation example B2.

As is clear from FIG. 18, if the value of L3 is not less than 5 micrometers, the dielectrophoresis force as the attractive force is given to the particles. Therefore, the particles are concentrated only at and around the center point O. On the other hand, if the value of L3 is 0 micrometers, the dielectrophoresis force is given as repulsive force to the particles, while the particles approaches the center point O along the stream of the fluid (namely, the sample solution) flowing through the flow path 103. Therefore, the particles fail to be concentrated.

Simulation Example B3

Figures 19, 20:
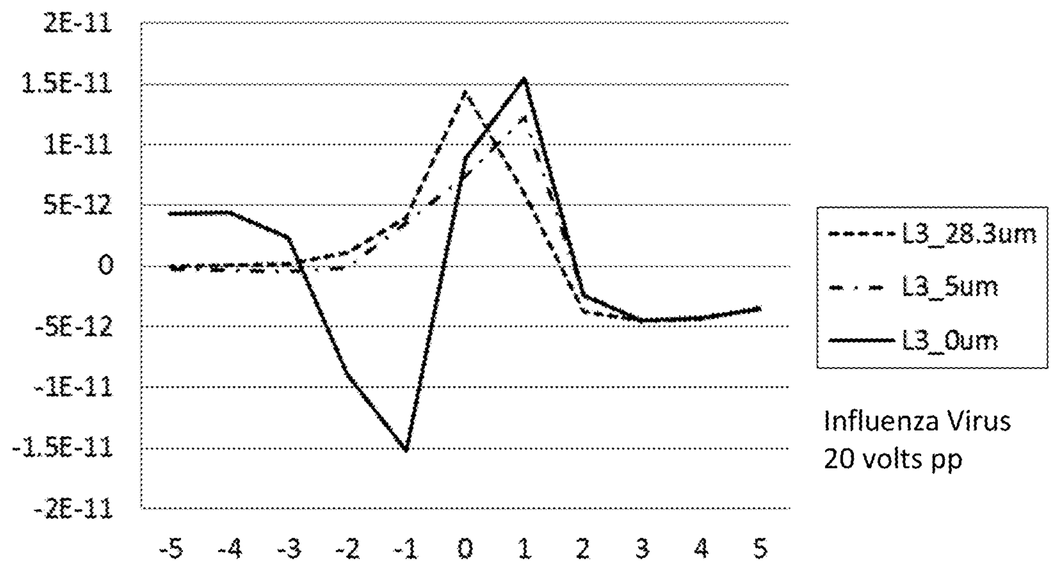
FIG. 19 is a graph showing the simulation results in the example B3.
FIG. 20 is a graph showing the simulation results in the example B4.

In the simulation example B3, a simulation similar to the simulation example B1 was carried out, except that the alternating voltage had 5 volts pp. FIG. 19 is a graph showing the results of the simulation example B3.

As is clear from FIG. 19, if the value of L3 is not less than 5 micrometers, the dielectrophoresis force as the attractive force is given to the particles. Therefore, the particles are concentrated only at and around the center point O. On the other hand, if the value of L3 is 0 micrometers, the dielectrophoresis force is given as repulsive force to the particles, while the particles approaches the center point O along the stream of the fluid (namely, the sample solution) flowing through the flow path 103. Therefore, the particles fail to be concentrated.

Simulation Example B4

In the simulation example B4, a simulation similar to the simulation example B1 was carried out, except that the alternating voltage had 20 volts pp. FIG. 20 is a graph showing the results of the simulation example B4.

As is clear from FIG. 20, if the value of L3 is not less than 5 micrometers, the dielectrophoresis force as the attractive force is given to the particles. Therefore, the particles are concentrated only at and around the center point O. On the other hand, if the value of L3 is 0 micrometers, the dielectrophoresis force is given as repulsive force to the particles, while the particles approaches the center point O along the stream of the fluid (namely, the sample solution) flowing through the flow path 103. Therefore, the particles fail to be concentrated.

Simulation Example B5

Figure 21:
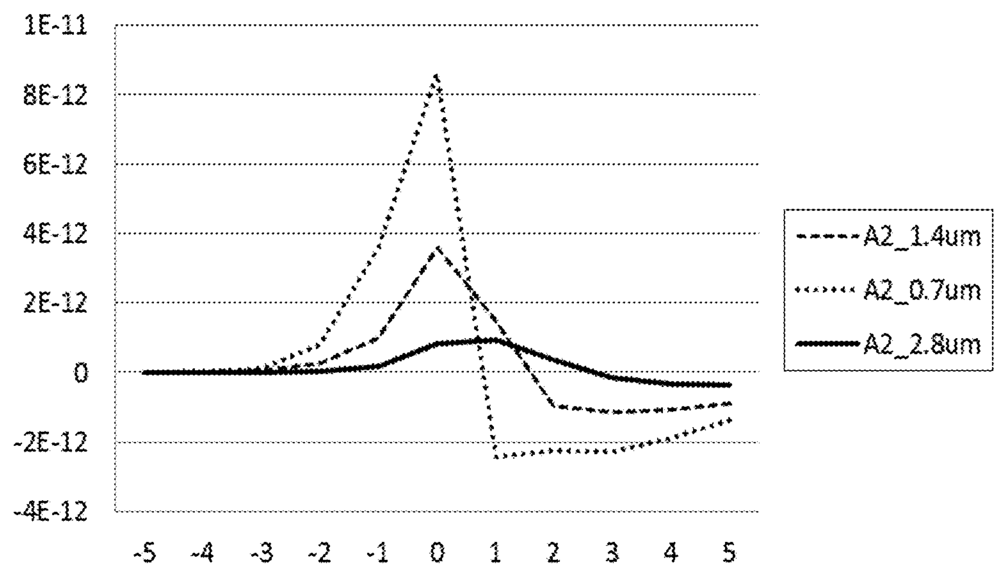
FIG. 21 is a graph showing the simulation results in the example B5.

In the simulation example B5, a simulation similar to the simulation example B1 was carried out, except that the value of A2 was 0.7 micrometers or 2.8 micrometers. FIG. 21 is a graph showing the results of the simulation example B5.

As is clear from FIG. 21, regardless of the value of A2, the dielectrophoresis force as the attractive force is given to the particles. Therefore, regardless of the value of A2, the particles are concentrated only at and around the center point O. The greater dielectrophoresis force as the attractive force is given to the particles with a decrease in the value of A2.

Simulation Example B6

Figure 22:
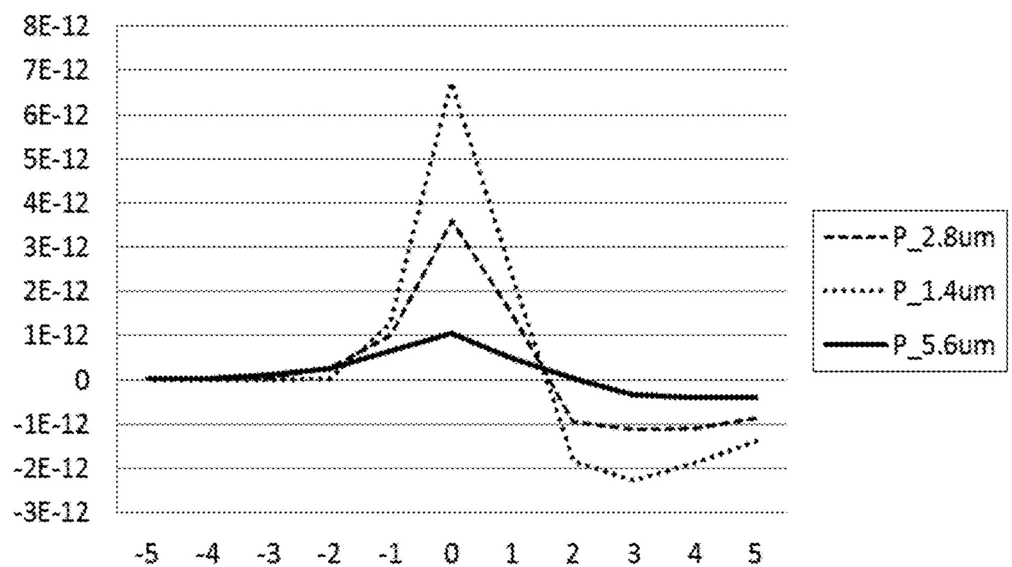
FIG. 22 is a graph showing the simulation results in the example B6.

In the simulation example B6, a simulation similar to the simulation example B1 was carried out, except that the value of P was 0.7 micrometers or 2.8 micrometers. FIG. 22 is a graph showing the results of the simulation example B6.

As is clear from FIG. 22, regardless of the value of P, the dielectrophoresis force as the attractive force is given to the particles. Therefore, regardless of the value of P, the particles are concentrated only at and around the center point O. The greater dielectrophoresis force as the attractive force is given to the particles with a decrease in the value of P.

Simulation Example B7

Figure 23:
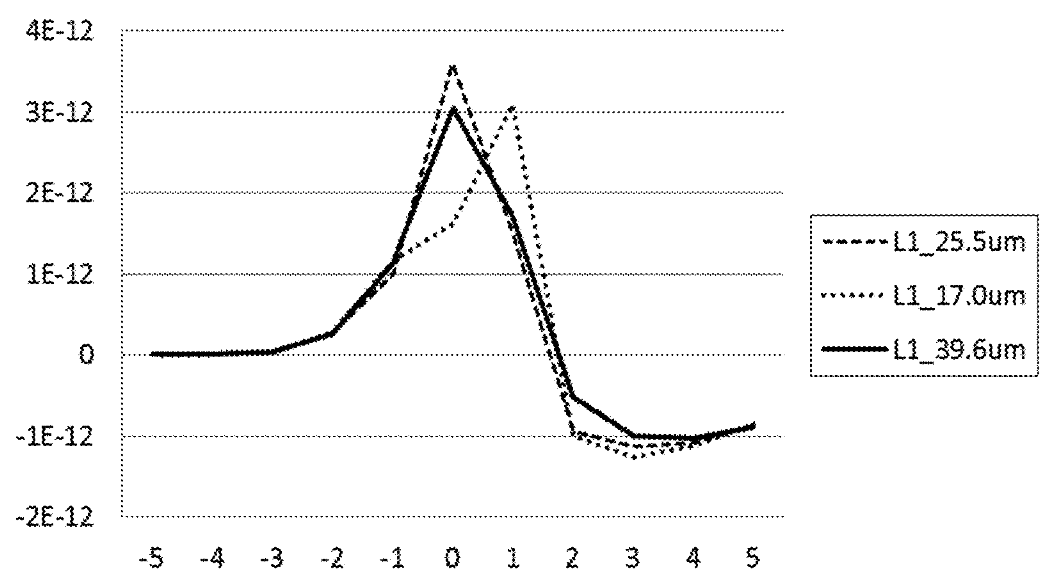
FIG. 23 is a graph showing the simulation results in the example B7.

In the simulation example B7, a simulation similar to the simulation example B1 was carried out, except that the value of L1 was 25.5 micrometers or 39.6 micrometers. FIG. 23 is a graph showing the results of the simulation example B7.

As is clear from FIG. 23, regardless of the value of L1, the dielectrophoresis force as the attractive force is given to the particles. Therefore, regardless of the value of L1, the particles are concentrated only at and around the center point O.

INDUSTRIAL APPLICABILITY

The present invention can be used for a sensor for concentrating a virus having low concentration.

REFERENTIAL SIGNS LIST

101 Inlet
102 Outlet
103 Flow path
110 First substrate
105 Second substrate
201 First comb-shaped electrode
202 Second comb-shaped electrode
301 First pillar electrodes
  301L Left-side first pillar electrode 301R Right-side first pillar electrode 302 Second pillar electrodes 302A Second pillar electrode A included in First pillar electrode line 302B Second pillar electrode B included in Second pillar electrode line 303*a* First pillar electrode line 303*b* Second pillar electrode line 303*c* Third pillar electrode line A1 Distance between Second vertex Q2 of Second pillar electrode A and Center point O A2 Distance between First vertex Q1 of Second pillar electrode B and Center point O H Height of Flow path L1 Length of First pillar electrode L2 Length of Second pillar electrode L3 Distance obtained by subtracting A2 from A1

LL Line

O Center point

P Line segment

P1 First vertex of First pillar electrode

P2 Second vertex of First pillar electrode

Q Line segment

Q1 First vertex of Second pillar electrode

Q2 Second vertex of Second pillar electrode

W Width of Flow path

U Region of Pillar electrode group

The invention claimed is:

1. A concentration device suitable for dielectrophoresis, comprising:

a first substrate;

a second substrate provided so as to face the first substrate;

a flow path formed between the first substrate and the second substrate;

a first pillar electrode line disposed in the flow path; and a second pillar electrode line disposed in the flow path, wherein:

the first pillar electrode line and the second pillar electrode line are parallel to an X-axis direction;

the first pillar electrode line and the second pillar electrode line include first pillar electrodes and second pillar electrodes;

each of the first pillar electrodes includes a first vertex P1 and a second vertex P2;

each of the second pillar electrode includes a first vertex Q1 and a second vertex Q2;

a line segment between the first vertex P1 and the second vertex P2 which are included in each of the first pillar electrodes is parallel to the X-axis direction;

a line segment between the first vertex Q1 and the second vertex Q2 which are included in each of the second pillar electrodes is parallel to a Y-axis direction;

the X-axis direction is perpendicular to the Y-axis direction in a top view;

a pillar electrode group is composed of:

a left-side first pillar electrode L selected from the first pillar electrodes included in the second pillar electrode line;

a right-side first pillar electrode R selected from the first pillar electrodes included in the second pillar electrode line;

a second pillar electrode A selected from the second pillar electrodes included in the first pillar electrode line; and a second pillar electrode B selected from the second pillar electrodes included in the second pillar electrode line;

the left-side first pillar electrode L and the right-side first pillar electrode R are adjacent to each other in a top view in such a manner that the second vertex P2 of the left-side first pillar electrode L and the first vertex P1 of the right-side first pillar electrode R face each other;

a line which passes through the second vertex Q2 of the second pillar electrode A and the first vertex Q1 of the second pillar electrode B is parallel to the Y-axis direction; and the following mathematical formula (I) is satisfied:

$$L3 \geq 5 \text{ micrometers} \quad \text{(I)}$$

where:

$$L3 = A1 - A2,$$

A1 represents a distance between the second vertex Q2 of the second pillar electrode A and a center point O;

A2 represents a distance between the first vertex Q1 of the second pillar electrode B and the center point O;

the center point O is an intersection point of a line segment P and a line segment Q, the line segment Q is a line segment between the second vertex Q2 of the second pillar electrode A and the first vertex Q1 of the second pillar electrode B; and the line segment P is a line segment between the second vertex P2 of the left-side first pillar electrode L and the first vertex P1 of the right-side first pillar electrode R.

2. A method for concentrating particles contained in a sample solution, the method comprising:

(a) preparing a concentration device according to claim 1; and (b) applying an alternating voltage between the first pillar electrodes and the second pillar electrodes, while the sample solution is caused to flow in a direction from the first pillar electrode line to the second pillar electrode line, to concentrate the particles only at and around the center point O.

3. The method according to claim 2, wherein each of the particles has a particle diameter of not more than 100 nanometers.

4. The method according to claim 2, wherein the alternating voltage has a voltage of not more than 20 volts pp.

5. The method according to claim 2, wherein the value of A2 is not more than 1.4 micrometers.

6. The method according to claim 2, wherein the line segment P has a length of not more than 2.8 micrometers.

7. The method according to claim 2, wherein the particles are influenza virus.

8. The method according to claim 2, wherein the particles are norovirus.

* * * * *